United States Patent [19]

Cottingham et al.

[11] 4,161,042
[45] Jul. 17, 1979

[54] ADJUSTABLE PROSTHETIC LIMB

[75] Inventors: Hugh V. Cottingham, Upper Montclair; Joseph Scrocco, West Orange, both of N.J.

[73] Assignee: BHN, Inc., Upper Montclair, N.J.

[21] Appl. No.: 845,185

[22] Filed: Oct. 25, 1977

[51] Int. Cl.$^2$ .............................................. A61F 1/08
[52] U.S. Cl. ........................................ 3/17 R; 3/21; 3/7
[58] Field of Search ................... 3/21, 17 R, 18, 2, 4, 3/6, 7

[56] References Cited

U.S. PATENT DOCUMENTS

| | | | |
|---|---|---|---|
| 514,225 | 2/1894 | Hershberger | 3/17 R X |
| 708,685 | 9/1902 | White | 3/6 UX |
| 1,144,681 | 6/1915 | Apgar | 3/17 R X |
| 1,995,442 | 3/1935 | Wolfe | 3/7 X |
| 2,908,016 | 10/1959 | Botko | 3/17 R |
| 3,098,239 | 7/1963 | Nader | 3/7 |
| 3,545,046 | 12/1970 | Colley | 3/17 R X |
| 3,707,731 | 1/1973 | Morgan | 3/7 X |
| 3,741,226 | 6/1973 | Urban | 135/86 X |

FOREIGN PATENT DOCUMENTS

| | | | |
|---|---|---|---|
| 323671 | 7/1920 | Fed. Rep. of Germany | 3/2 |
| 152656 | 12/1955 | Sweden | 3/17R |
| 127451 | 6/1919 | United Kingdom | 3/21 |

Primary Examiner—Clifford D. Crowder
Attorney, Agent, or Firm—Blum, Moscovitz, Friedman & Kaplan

[57] ABSTRACT

A light-weight, universally sized prosthetic appliance for supporting a person having a residual limb. The prosthetic limb includes a socket adapted to define a selectively adjustable sleeve for receiving and securing a residual limb therein. The adjustable sleeve includes an ischial bearing member for supporting the person's weight. An elongated support member is adjustably and releaseably secured to the socket for selectively adjusting the length of the prosthetic limb and the utility thereof.

31 Claims, 18 Drawing Figures

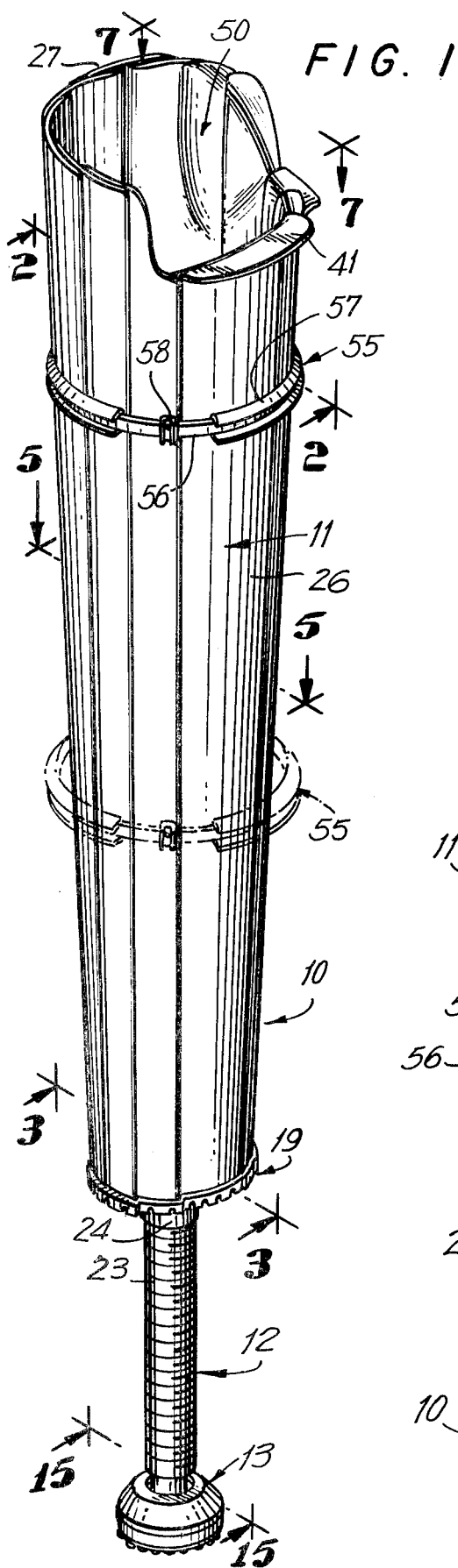
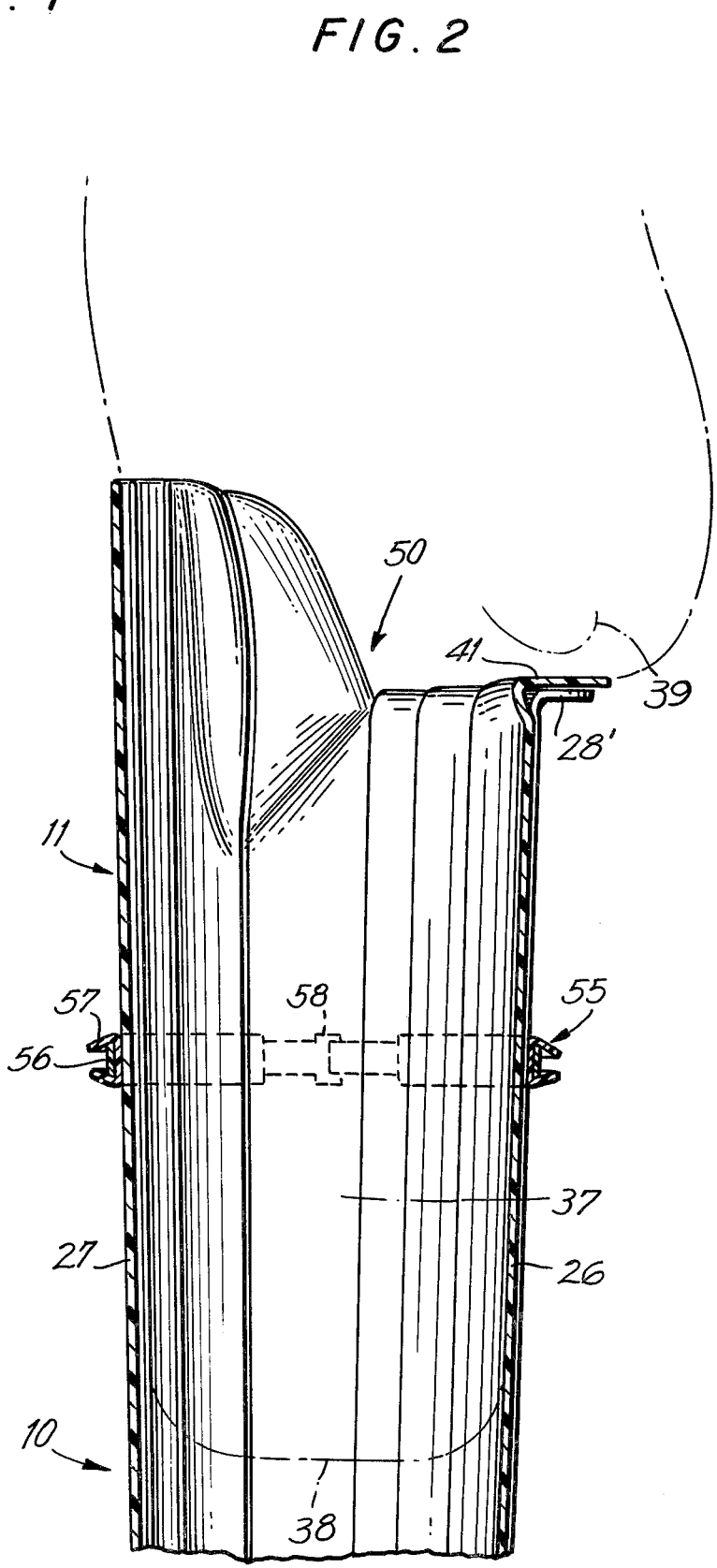

FIG. 5
FIG. 6
FIG. 7
FIG. 8
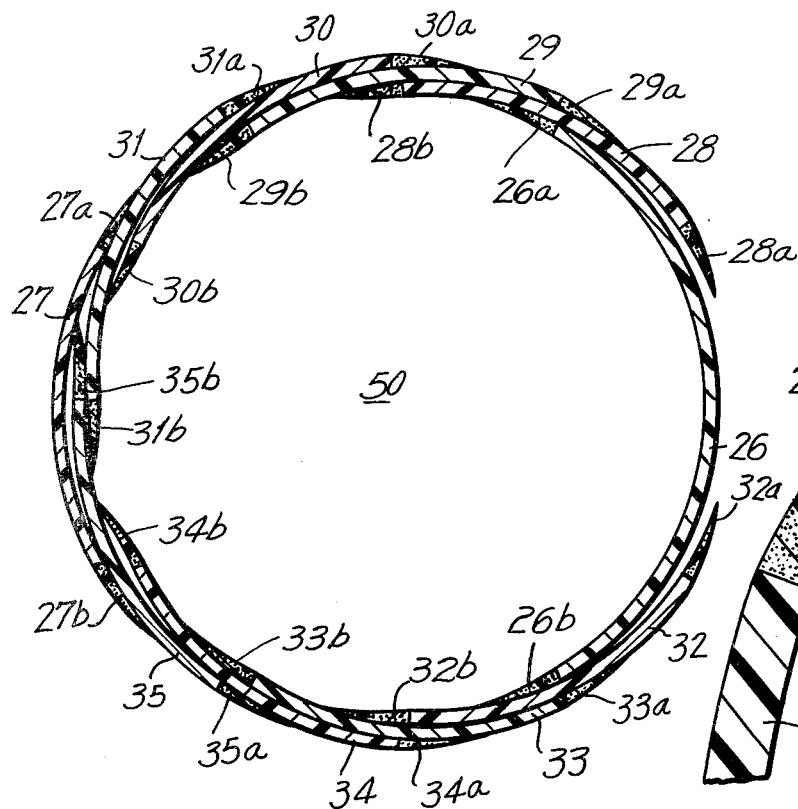
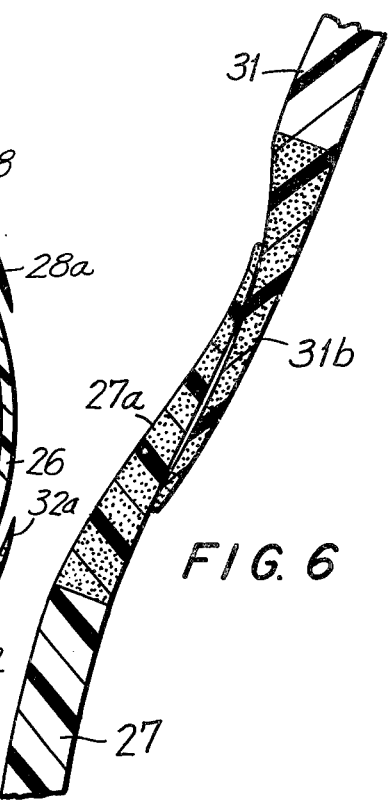
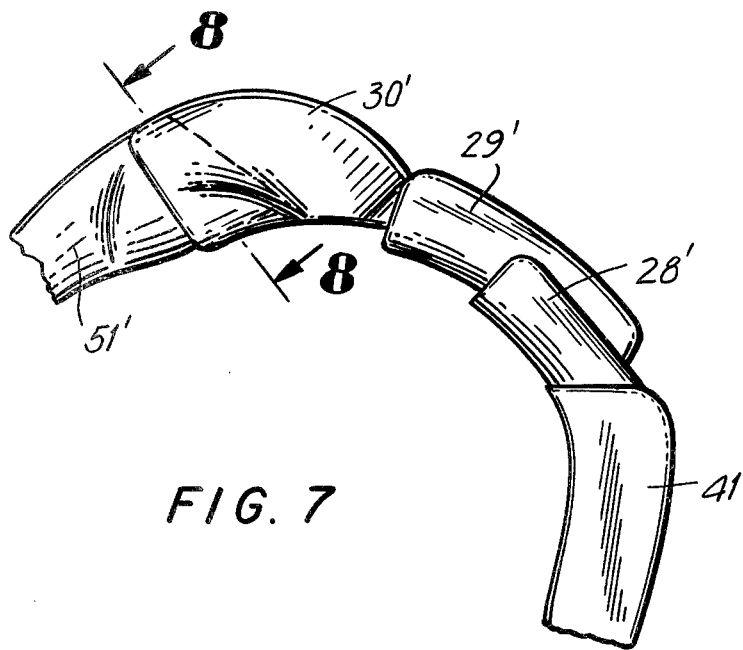
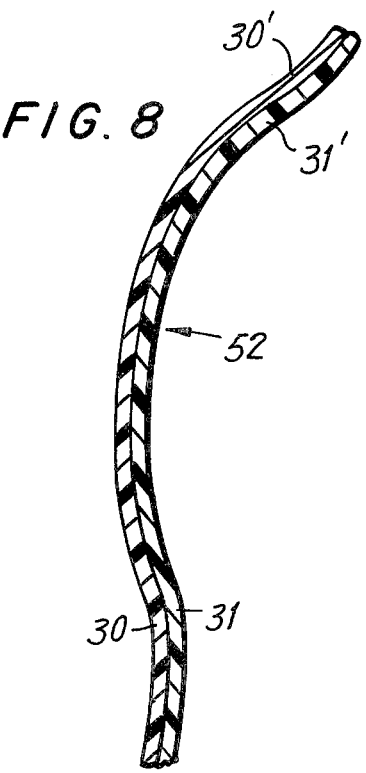

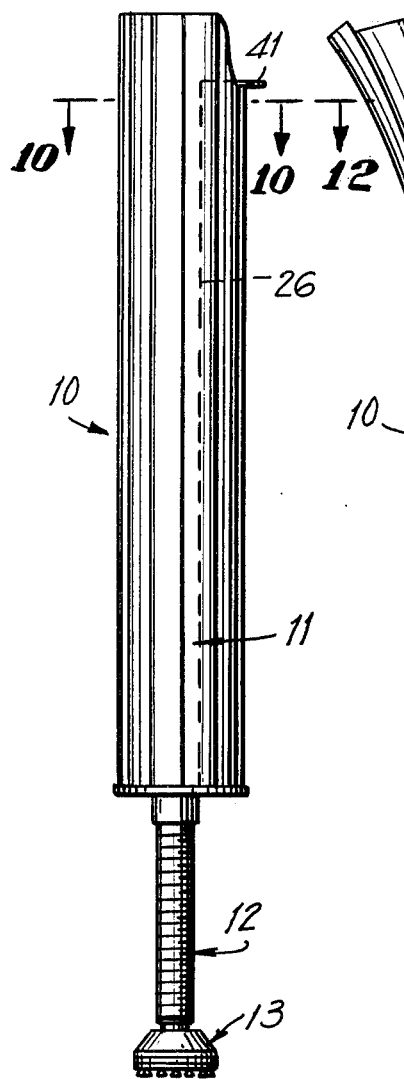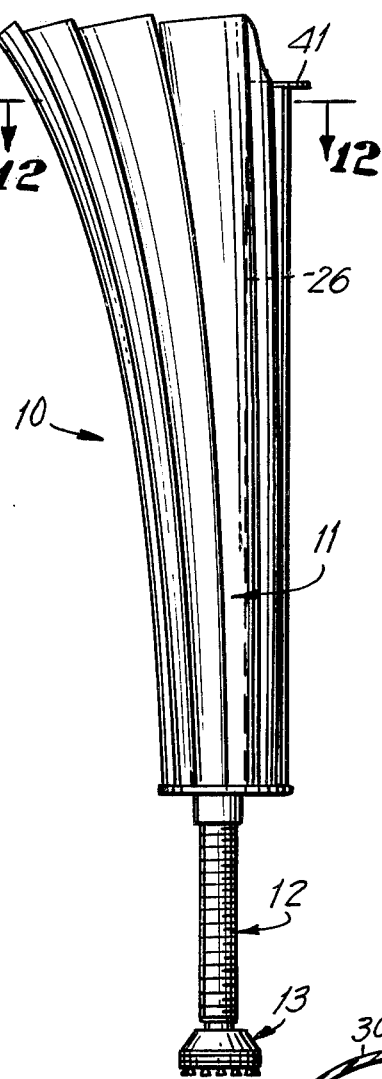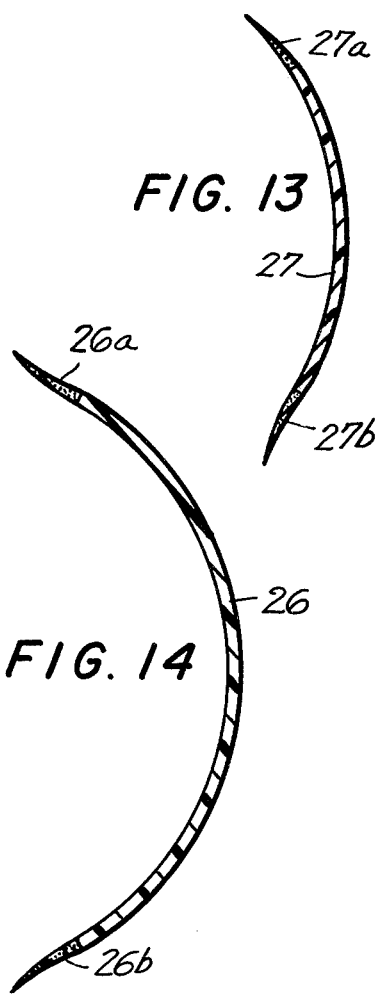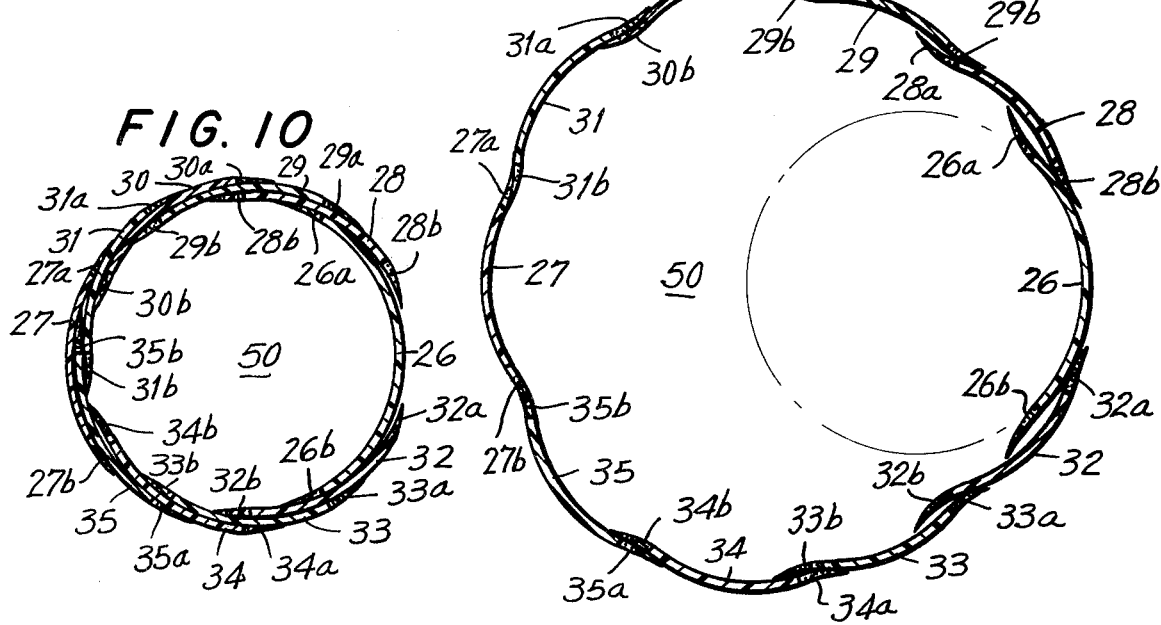

U.S. Patent  Jul. 17, 1979  Sheet 5 of 5  4,161,042
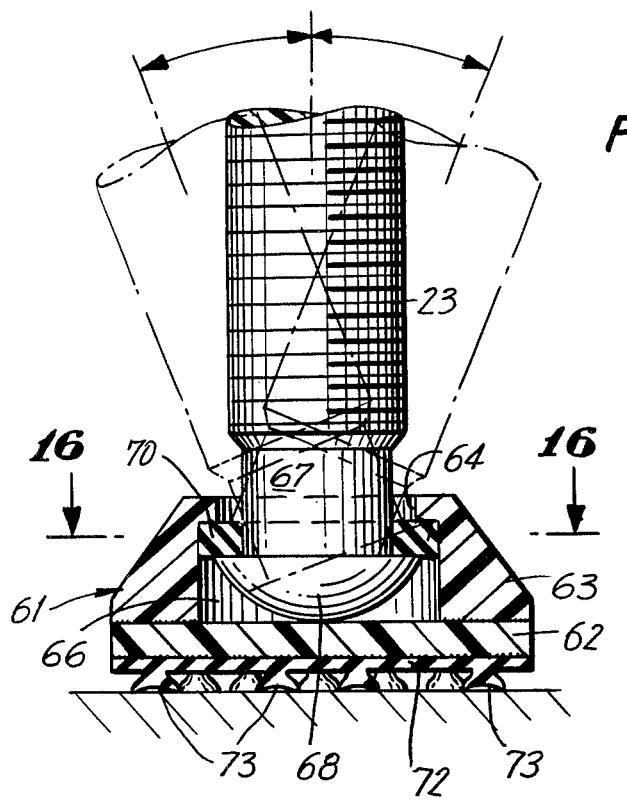
FIG. 15
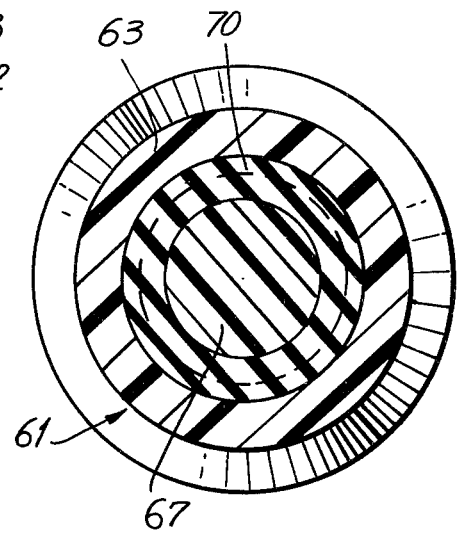
FIG. 16
FIG. 17
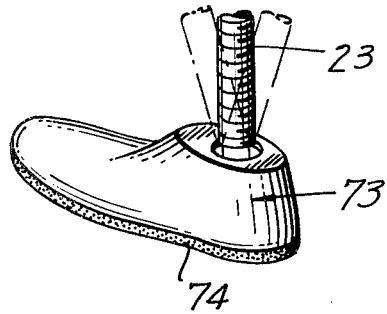
FIG. 18
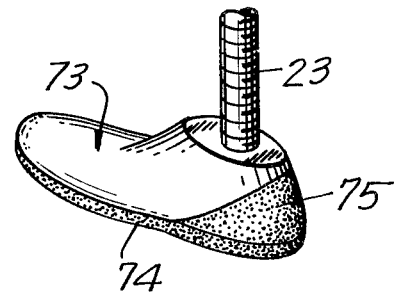

ADJUSTABLE PROSTHETIC LIMB

BACKGROUND OF THE INVENTION

This invention is directed to a light-weight, universally sized prosthetic limb for supporting a person having a residual limb, and in particular to a prosthetic limb having an adjustable socket and support for receiving and supporting the residual limb of persons of varying height and weight.

Heretofore, persons that have suffered the loss of a portion of their leg, by amputation, and have been left with a residual limb, have resorted to the use of prosthetic appliances, and in particular custom made prosthetic limbs for support and ambulation. These prosthetic limbs must be custom made because of the individual deviation in height and weight of each person, and more importantly, the individual idiosyncratic physiological condition of the residual limb including, but not limited to, the length of the residual limb, the possible weight fluctuations thereof and the atrophy of the limb that occurs after amputation. An additional physiologic condition that must be taken into account in women is menstral weight fluctuation.

Because each prosthetic limb must be custom made to accommodate the individual idiosyncratic physiologic conditions noted above, such limbs cannot be mass produced, thereby considerably increasing the cost thereof. Moreover, because custom made prosthetic limbs are made of materials that can be shaped to accommodate the individual idiosyncratic physiologic conditions noted above, these materials (metal, wood, etc.) are subject to environmental degradation such as by rusting, rotting, warping and fatigue.

Because custom made prosthetic limbs are formed of materials that are likely to rust, warp and fatigue, they are incapable of use in routine hygiene activities such as washing and showering. Because most custom made prosthetic limbs cannot be utilized to perform such activities, the upper arms must be utilized for support and balance, thereby rendering it difficult for the amputee to complete hygiene activities that are easily completed by a non-amputee. Accordingly, a prosthetic limb capable of adjusting to all physiologic variations of the amputee population such as the length of the residual limb, diameter of the residual limb, and fluctuations likely to result therein, and that is environmentally resistant and is easily secured to the limb would eliminate many of the disadvantages noted above.

SUMMARY OF THE INVENTION

Generally speaking, in accordance with the instant invention, a prosthetic limb for supporting a person having a residual limb is provided. The prosthetic limb includes a socket adapted to define a selectively adjustable sleeve for receiving and securing a residual limb therein. The adjustable sleeve includes an ischial bearing member for supporting a person's weight. An elongated support is releaseably and adjustably secured to the socket for selectively adjusting the length and utility of the prosthetic limb.

In an exemplary embodiment, the elongated support member can include a universally joined skid resistant pod at the distal end thereof, for permitting a person to perform hygiene activities such as washing and showering in a safe and comfortable manner. Alternatively, a prosthetic appliance for facilitating ambulation, such as a swivel ankle foot, can be secured to the distal end of the elongated support member.

Accordingly, it is an object of the instant invention to provide a light-weight, inexpensive and adjustable prosthetic limb.

A further object of the instant invention is to provide an improved prosthetic limb that is adjustable to the physiological variations in length, diameter and taper of residual limbs resulting from the inherent physical differences likely to be found among the amputee population.

Still a further object of the instant invention is to provide an improved prosthetic limb that is strong, safe, environment proof and medically acceptable.

Still other objects and advantages of the invention will in part be obvious and will in part be apparent from the specification.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 1 is a perspective view of a prosthetic limb for use on slippery surfaces, constructed in accordance with a preferred embodiment of the instant invention;

FIG. 2 is a sectional view taken along line 2—2 of FIG. 1;

FIG. 5 is a sectional view taken along line 5—5 of FIG. 1;

FIG. 6 is an enlarged sectional view of the overlapping relationship of the struts depicted in FIG. 12;

FIG. 7 is a sectional view taken along line 7—7 of FIG. 1;

FIG. 8 is a sectional view taken along line 8—8 of FIG. 7;

FIG. 9 is an elevational view of the prosthetic limb depicted in FIG. 1, when not in use;

FIG. 10 is a sectional view taken along line 10—10 of FIG. 9;

FIG. 11 is an elevational view of the prosthetic limb depicted in FIG. 1, when in use;

FIG. 12 is a sectional view taken along line 12—12 of FIG. 11;

FIG. 13 is a transverse sectional view of the forward strut of the prosthetic limb illustrated in FIG. 1;

FIG. 14 is a transverse sectional view of the ischial bearing strut of the prosthetic limb depicted in FIG. 1;

FIG. 15 is a sectional view taken along line 15—15 of FIG. 1;

FIG. 16 is a sectional view taken along line 16—16 of FIG. 15;

FIG. 17 is a perspective view of a swivel ankle prosthetic foot for use with the prosthetic limb of the instant invention; and FIG. 18 is a perspective view of a solid ankle cushioned heel prosthetic foot for use with the prosthetic limb of the instant invention.

DETAILED DESCRIPTION OF THE PREFERRED EMBODIMENTS

Reference is first made to FIG. 1, wherein a prosthetic leg, generally indicated as 10, for use on slippery surfaces likely to be found in bathrooms, swimming pools and the like, is depicted. The prosthetic leg includes a socket assembly, generally indicated as 11, for receiving a residual limb, a height adjustable support assembly, generally indicated as 12, releasably and adjustably secured to the socket assembly, and a skid resistant pod assembly, generally indicated as 13, universally joined to the height adjustable support assembly.

Figure 3:
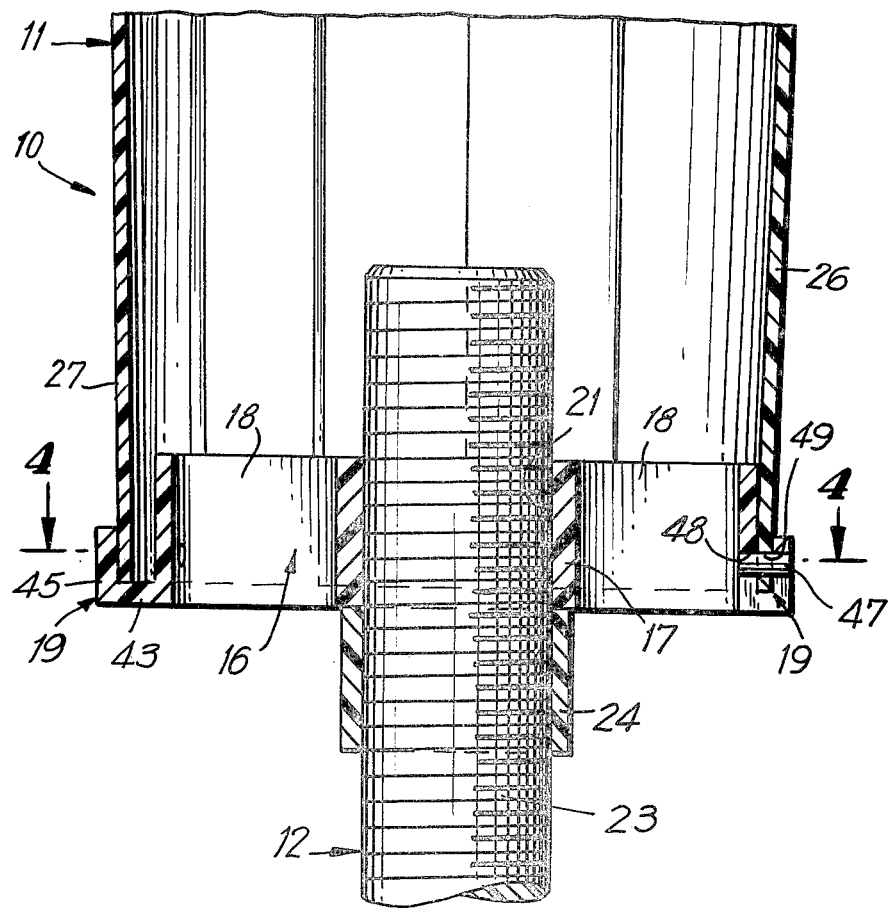
FIG. 3 is a sectional view taken along the line 3—3 of FIG. 1.
Figure 4:
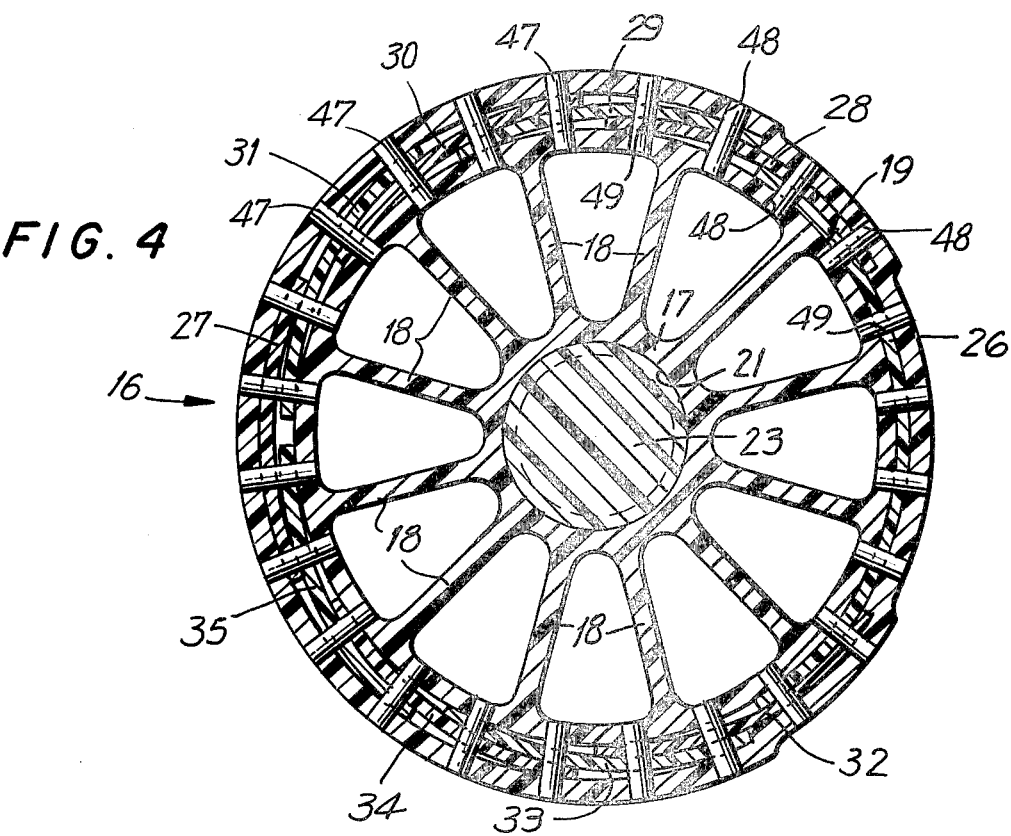
FIG. 4 is a sectional view taken along line 4—4 of FIG. 3.

Referring now to FIGS. 3 and 4, the socket assembly 11 includes a base plate, generally indicated as 16, which base plate includes a support hub 17 having integrally formed spokes 18 emanating therefrom. The spokes are integrally formed with and support an annular receptacle 19 to be described in greater detail below. The support hub 17 includes an elongated tapped opening 21 for receiving an elongated adjustable threaded support rod 23 therein. The elongated threaded support rod is part of the height adjustable support assembly 12, and is fixedly positioned with respect to the support hub 17 and, hence, base plate 16, by means of a threaded locking nut 24 when the locking nut is rotated into abutment with the support hub 17. In the exemplary embodiment depicted in FIG. 1, pod assembly 13, for providing skid resistance on wet surfaces, is secured to the distal end of the adjustable support rod 23 in order to permit the prosthetic limb to be supported on a wet surface. It is noted that the particular pod assembly, illustrated in FIG. 1, is explained hereinafter in detail and that the prosthetic limb of the instant invention is not limited to the particular pod assembly, illustrated in FIG. 1, or the particular application provided thereby.

In addition to the base plate 16, the socket assembly is comprised of a plurality of elongated struts secured to the base plate in order to define an adjustable sleeve that functions as an adjustable quadrilateral type socket in a manner described in detail below. Referring particularly to FIGS. 1 through 14, ten elongated struts including ischial bearing strut 26, forward strut 27 and side struts 28 through 35, are secured in the annular receptacle 19 in an overlapping configuration to define a sleeve. Each of the elongated struts are formed of a rigid, non-elastomeric plastic with a transverse curvature formed therein to impart structural integrity thereto. Each strut further includes integrally formed elastomeric flexible edges designated by the suffix a and b following each of the reference numerals 26 through 35, which flexible edges extend almost the entire lengthwise extent of each strut.

By way of reference, a person's shape is illustrated in FIG. 2, in phantom, with the distal end 38 of the residual limb 37 being inserted into the prosthetic leg and the ischial tuberosity 39 being supported by the ischial bearing strut 28. The ischial bearing strut 26 has the largest transverse dimension and includes a bearing portion 40 and an ischial shelf 41 projecting from the bearing portion 40 at approximately a right angle with respect thereto. The ischial bearing strut 26 is utilized to support substantially all of the weight of the person, which weight is applied at the position whereat the ischial tuberosity rests upon the ischial shelf. The remaining struts, including forward strut 27, and side struts 28 through 35, define a radially adjustable sleeve 50 for receiving different residual limbs having varying radial dimensions and tapers, and for developing a lateral force that is applied to the residual limb in order to align the ischial bearing strut 26, and in particular, the bearing portion thereof with the ischial tuberosity.

As is particularly illustrated in FIGS. 3 and 4, each of the struts 26 through 35 are secured in the annular receptacle in overlapping fashion in order to provide the sleeve arrangement noted above. Specifically, the annular receptacle 19 includes a bottom wall 43, and inner side wall 44 and an outer side wall 45, for receiving and securing the ends of the struts therein. It is noted that in the embodiment depicted in FIGS. 3 and 4, the flexible edges have been removed in order to facilitate the securing of the struts into the base plate. Accordingly, the ischial bearing strut 26 is disposed against the inner side wall of annular receptacle 19 and is overlapped on a first side by side strut 28, and on the other side by side strut 32. Thereafter, struts 29, 30 and 31 are secured in the annular receptacle 19 in the same manner as struts 32, 33, 34 and 35 so that the side edge proximate to the ischial bearing strut 26 is on the outside of the strut closer to the ischial bearing strut and the side edge that is away from the ischial bearing strut is disposed inside of the side strut, further away from the ischial bearing strut. Accordingly, by this relationship, the side struts 31 and 35 overlap on the inside of the forward strut 27. It is noted that each of the struts 26 through 38 are anchored in the base plate by anchoring pins 47 that are friction fit in openings 48 formed in the inner and outer side walls 44 and 45 of the annular receptacle 19 and further openings 49 formed in the portions of the struts secured between the inner side walls and outer side walls. The overlapping relationship between the adjacent struts permits at least two anchoring pins to be secured in the overlap between adjacent strut members. It is noted that an adhesive can also be utilized in addition to, or in lieu of, the anchoring pins in order to anchor the struts to the base plate.

Accordingly, the overlapping relationship of the struts 26 through 35 define sleeve 50 for receiving the residual limb therein. However, the upper portions of certain of the struts are shaped in order to define an adjustable quadrilateral-type socket for receiving the residual limb. Although the prosthetic leg, illustrated in FIG. 1, is for a left limb, it is noted that a prosthetic leg for the right limb would be identical to, but in mirror image to, the prosthetic leg depicted in FIG. 1. In order to complete the adjustable quadrilateral-type socket, overlapping side struts 28 through 31 each include arcuate or bent portions 28' through 31', which portions overlap with respect to each other in the manner depicted in FIG. 7 to define a scarpular triangle, illustrated as 52, in FIG. 8. Accordingly, the struts are shaped to define a quadrilateral-type socket for receiving a residual limb. It is noted, however, that unlike custom made prosthetic limbs utilizing a suction grip, it is not necessary for the quadrilateral-type socket to be custom fit to the size and shape of the residual limb.

In order to secure the sleeve about the residual limb, a closed adjustment loop, generally indicated as 55, is provided. The adjustment loop 55 includes a nylon band 56 secured in a U-shaped hand grip 57 with the opposite ends of the nylon band being secured together by a unidirectional nylon locking member 58. The U-shaped hand grip permits manual gripping when the adjustable loop is pulled up in order to effect tightening of the adjustable socket in a manner to be discussed in greater detail below. In order to avoid the necessity of providing a multiplicity of adjustment loops of various sizes, the unidirectional nylon locking member 58 permits the circumferential adjustment of the loop. Once the circumference of the adjustment loop is determined, a change in the elevation of the loop will change the radial dimension of the sleeve formed by the respective struts.

As aforenoted, each of the struts includes a flexible edge integrally formed with respect thereto. Moreover, each of the flexible edges is radiused inwardly or outwardly depending upon the manner in which it overlaps with the member adjacent thereto. For example, flexible edges 26a and 26b are radiused outwardly and are disposed inwardly of the flexible edges 28b and 32a, respectively, of adjacent struts 28 and 32. Similarly, flexible edge 28b is radiused inwardly since same is disposed on the outside in overlapping relationship with ischial bearing strut 26a. The flexible edges on each of the struts provides overlap between adjacent struts as the adjustable socket increases in diameter as a result of the residual limb being disposed therein. Additionally, the flexible side edges of each strut permit smooth accommodation of adjacent struts to each other as the diameter of the sleeve increases and the taper of the sleeve changes. This is best illustrated in FIG. 12, wherein a sectional view of the prosthetic leg illustrates the manner in which the overlapping struts expand and define a larger dimensional sleeve when the residual limb is disposed in the prosthetic leg.

Accordingly, prior to use, the prosthetic leg, depicted in FIG. 5, appears in the manner depicted in FIG. 9 and FIG. 10, with the ischial bearing strut 26 disposed substantially perpendicular with respect to the base plate, and with each of the remaining struts forming a small, substantially circular path therearound. However, when the residual limb is disposed in the sleeve 50, in the manner illustrated in FIG. 2, and the adjustable loop 55 is elevated in order to secure each of the struts around the residual limb, each of the struts 27 through 35, with the exception of the ischial bearing strut 26, will be laterally displaced in the manner depicted in FIGS. 11 and 12, to thereby define a larger diametered, albeit not circular, shaped sleeve. As illustrated in FIG. 11, the ischial bearing strut 26 remains approximately perpendicular with respect to the base plate 16, when the residual limb is disposed in the prosthetic leg, in order to assure that the ischial shelf 41 supports the ischial tuberosity and, hence, substantially all of the weight that is supported by the prosthetic leg. It is noted that the remaining struts expand away from the ischial bearing strut and develop a radial force against the residual limb and thereby force the ischial bearing strut into alignment with the ischial tuberosity. Additionally, the remaining struts also serve to translate the stress of the bearing load on the ischial bearing strut proportionately about the base plate. Accordingly, the adjustable sleeve defined by the overlapping struts permit a residual limb of any length and thickness to be disposed in the sleeve, with the sleeve being adjusted to accommodate to the thickness of the limb and provide an appropriate taper therefor. Moreover, in the event that the residual limb were to atrophy, or in the alternative, during a woman's menstral cycle the dimension of the woman's leg were to temporarily increase, the size of the adjustable sleeve can be easily varied by changing the elevation of the adjustment loop.

It is noted that the entire prosthetic leg can be formed of light-weight synthetic materials. For example, each of the struts can be formed of a polyvinyl chloride resin. The base plate rod and the skid resistant pod assembly, described in detail below, can be formed of a polycarbonate resin. It is noted that any other light-weight environment proof material may also be used in order to form the prosthetic leg.

Reference is now made to FIGS. 15 and 16, wherein the skid-resistant pod assembly is depicted. Specifically, the pod assembly includes a pod, generally indicated as 61, having a base 62 and a side wall 63 forming an opening 64 and recessed chamber 65 therein, for receiving the distal end of the support rod 23. The support rod 23 includes a recessed shaft 67 having an integrally formed, substantially hemispherically shaped rocking head 68 at the end thereof. The rocking head 68 is received in the recessed chamber 65, defined by side wall 63, and is secured therein and permitted to define a universal swivel coupling (illustrated in phantom) between the rocking head and the pod 61, by means of a neoprene washer 70. A rubberized suction pad 72, having a plurality of suction cups 73 formed thereon, is secured to the bottom surface of the base 62 in order to provide a skid resistant surface. By utilizing the skid-resistant pod from the same environment proof materials as the height adjustable support assembly and/or socket assembly, a prosthetic leg that is particularly suitable for use on wet and slippery surfaces is provided. For example, an amputee wearing a prosthetic leg of the type depicted in FIG. 1 through FIG. 16, would be able to take a shower without fear of slipping or sliding on the smooth wet surfaces of the shower. Moreover, by forming the prosthetic leg of synthetic light-weight materials, not only is the shower leg not damaged by the water, but the amputee's arms are freed in the shower to permit normal hygiene activities to be completed.

It is noted, however, that the prosthetic limb of the instant invention is not limited to utilizing a skid-resistant pod, and instead can utilize conventional prosthetic foot appliances, of the type depicted in FIG. 17 and 18, for daily use. For example, in FIG. 17, a swivel action foot 73, having a foamed rubber heel and sole 74, can be secured to the support rod in the same manner as the pod assembly 13. Alternatively, another type of prosthetic foot, known as a solid ankle cushioned heel, having a foamed heel 75 and rubber heel and sole 74, could be fixedly secured to the support rod 23.

Accordingly, the prosthetic leg of the instant invention is particularly characterized by the manner in which same can be adjusted to accommodate all variations found among the amputee population. For example, the length of the residual limb, diameter of the residual limb and taper of the residual limb are accommodated by the selectively adjustable sleeve defined by the overlapping struts. Similarly, a person's height is readily adjusted for by releasing the locking nut 24 and, hence, shortening or lengthening the positioning of the adjustable support rod with respect to the base plate. Moreover, individual idiosynchratic physiological conditions such as weight fluctuation and limb atrophy are accommodated by the use of the adjustment loop and the fact that same need only be raised and lowered in order to effect adjustment of the size of the socket. Finally, the construction of the prosthetic leg permits same to be mass produced from synthetic materials and, hence, utilized in bathrooms, swimming pools and other wet surfaces that heretofore would have been dangerous to the amputee and would have had a degrading effect on the prosthetic appliance.

It will thus be seen that the objects set forth above, among those made apparent from the preceding description, are efficiently attained and, since certain changes may be made in the above construction without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A prosthetic appliance for supporting a person having a residual lower limb comprising a socket means including a base plate, and a plurality of struts, each of said struts being secured in said base plate in overlapping relationship with respect to each other to define a selectively adjustable sleeve for receiving and securing a residual lower limb therein, said adjustable sleeve including an ischial bearing means for supporting a person's weight so that said selectively adjustable sleeve is adapted to be diametrically varied to receive a residual lower limb and to radially apply pressure to said residual lower limb and thereby stabilize the position of said ischial bearing means with respect to said person, and an elongated support means with respect to said person, and an elongated support means adjustably secured to said socket means for selectively adjusting the length of said prosthetic appliance.

2. A prosthetic appliance as claimed in claim 1, wherein said ischial bearing means is a strut.

3. A prosthetic appliance as claimed in claim 2, wherein said ischial bearing strut includes an elongated bearing portion having a curved lateral cross-section, each of said remaining struts defining said adjustable sleeve also having a curved lateral cross-section, whereby said overlapping struts define a substantially circular adjustable sleeve.

4. A prosthetic appliance as claimed in claim 3, wherein at least a portion of each overlapping edge of said struts are flexible and are integrally formed with respect to the remaining portion of said strut.

5. A prosthetic appliance as claimed in claim 4, wherein each flexible edge that overlaps the outer surface of an adjacent strut is radiused inwardly, and wherein each flexible edge of a strut that overlaps the inner surface of an adjacent strut is radiused outwardly.

6. A prosthetic appliance as claimed in claim 3, wherein said plurality of struts includes a forward strut and at least four side struts, a first side edge of at least two of said side struts being disposed in overlapping relationship with said ischial bearing strut, with the side edges of said ischial bearing strut being disposed on the inside of said side struts formed in overlapping relationship with respect thereto.

7. A prosthetic appliance as claimed in claim 6, wherein said further side struts having overlapping side edges nearer to the ischial bearing strut are positioned outside of the adjacent side edges of the struts nearer to said ischial bearing strut, said forward strut being disposed outside of and in overlapping relationship with respect to the side struts, to thereby complete said adjustable sleeve.

8. A prosthetic appliance as claimed in claim 7, wherein said ischial bearing strut includes a projecting flange portion defining an ischial shelf, and wherein said side struts on at least one side of said ischial bearing strut are curved at the free ends thereof, to thereby define an adjustable quadrilateral type socket.

9. A prosthetic appliance as claimed in claim 3, wherein said socket includes an adjustment loop disposed around the overlapping struts for selectively adjusting the diametric size of the sleeve, by changing the elevational position of said loop when a residual limb is disposed in said sleeve.

10. A prosthetic appliance, as claimed in claim 2, wherein said ischial bearing strut is provided with a lateral dimension that is larger than the remaining struts defining said adjustable sleeve.

11. A prosthetic appliance as claimed in claim 1, wherein said elongated support means includes a rod positionally secured to said base plate to permit the positioning of the rod to be varied with respect to said base plate and locking means disposed on said rod for fixedly positioning same with respect to said base plate.

12. A prosthetic appliance as claimed in claim 11, and including a skid-resistant pod having a skid-resistant surface universally joined to said support means for preventing said prosthetic appliance from sliding when said skid-resistant surface of said pod is disposed against a given surface.

13. A prosthetic appliance as claimed in claim 11, and including a prosthetic foot secured to said elongated support means.

14. A prosthetic appliance as claimed in claim 13, wherein said prosthetic foot includes universal coupling means for permitting said prosthetic foot to be coupled to said support means and to swivel with respect thereto.

15. A prosthetic appliance for supporting a person having a residual lower limb comprising a socket means including a base plate and a plurality of struts, each of said struts being secured in said base plate in overlapping relationship with respect to each other to define a selectively adjustable sleeve, one of said struts being an ischial bearing strut, said ischial bearing strut including an elongated bearing portion having a curved lateral cross-section to impart strength thereto, said ischial bearing strut further including a substantially flat projecting flange defining an ischial shelf, whereby a person's ischial tuberosity rests upon the ischial shelf when a residual lower limb is inserted into said prosthetic appliance, and an elongated support means adjustably secured to said socket means for selectively adjusting the length of said prosthetic appliance.

16. A prosthetic appliance, as claimed in claim 15, wherein said elongated bearing portion of said ischial bearing strut is disposed in said support plate at an angle that is normal to the radial dimension thereof, said ischial shelf being substantially disposed in a plane that is normal to the elongated orientation of said elongated bearing portion to thereby permit ambulation of said residual lower limb when same is supported in said sleeve.

17. A prosthetic appliance for supporting a person having a residual lower limb comprising a socket means adapted to define a selectively adjustable sleeve for receiving and securing a residual lower limb therein, said socket means being comprised of a support plate, and a plurality of elongated struts secured to said support plate in overlapping relationship with respect to each other to define said adjustable sleeve one of said struts defining an ischial bearing strut having a curved lateral cross-section, and an elongated support means adjustably secured to said support plate for selectively adjusting the length of said prosthetic appliance.

18. A prosthetic appliance as claimed in claim 17, wherein each of said struts has a curved lateral cross-section whereby said overlapping struts define a substantially circular adjustable sleeve.

19. A prosthetic appliance as claimed in claim 18, and including an adjustment loop secured around said overlapping struts for selectively varying the diametric size of said circular adjustable sleeve formed by said overlapping struts in response to said loop being longitudinally displaced with respect to said struts.

20. A prosthetic appliance as claimed in claim 19, wherein at least a portion of each of said overlapping edges of said struts are flexible.

21. A prosthetic appliance as claimed in claim 20, and including a skid-resistant pod means secured to the elongated support means for supporting said prosthetic appliance on slippery surfaces.

22. A prosthetic appliance as claimed in claim 21, wherein said skid-resistant pod means is universally joined to said elongated support means in order to permit said elongated support means to be swiveled with respect to said pod means.

23. A prosthetic appliance as claimed in claim 22, wherein said skid-resistant pod means includes a substantially flat bottom surface, and a plurality of suction means secured to said bottom surface for preventing said pod means from slipping on smooth and wet surfaces.

24. A prosthetic appliance as claimed in claim 20, and including a prosthetic foot means adapted to be secured to said elongated support means, to thereby permit said prosthetic appliance to function as a prosthetic leg.

25. A prosthetic appliance as claimed in claim 24, wherein said prosthetic foot means is a swivel action foot.

26. A prosthetic appliance as claimed in claim 24, wherein said prosthetic foot means is a solid ankle cushioned heel foot that is fixedly secured to said elongated support means.

27. A prosthetic appliance for supporting a person having a residual lower limb comprising a socket means adapted to define a selectively adjustable sleeve for receiving and securing a residual lower limb therein, said socket means including a plurality of elongated struts, each of said struts being disposed in overlapping relationship to define an adjustable sleeve, each of said struts having a curved lateral cross-section, an elongated portion along the entire lengthwise extent of each strut having a predetermined structural integrity, and at least one longitudinal edge of each said strut being flexibly non-structural in order to create a smooth and continuous sleeve that is adapted to contour about a lower residual limb in non-uniform fashion, one of said struts defining an ischial bearing member, and an elongated support means adjustably secured to said socket means.

28. A prosthetic appliance as claimed in claim 27, wherein said ischial bearing member includes an ischial bearing portion and an ischial bearing shelf, said ischial bearing portion being normal to the ground, said ischial bearing shelf being disposed substantially at a right angle to the lengthwise extent of said ischial bearing portion.

29. A prosthetic appliance, as claimed in claim 28, wherein said plurality of struts includes a forward strut and at least four side struts, a first side edge of at least two of said side struts being disposed in overlapping relationship with said ischial bearing strut, with the side edges of said ischial bearing strut being disposed on the inside of said side struts formed in overlapping relationship with respect thereto.

30. A prosthetic appliance, as claimed in claim 29, wherein said further side struts having overlapping side edges nearer to the ischial bearing strut are positioned outside of the adjacent side edges of the struts nearer to said ischial bearing strut, said forward struts being disposed outside of and in overlapping relationship with respect to the side struts, to thereby complete said adjustable sleeve.

31. A prosthetic appliance for supporting a person having a residual lower limb comprising a socket means having a support plate and a plurality of overlapping struts, one of said struts defining an ischial bearing member, said ischial bearing member having a bearing portion that is normal to the radial dimension of said base plate, and an ischial shelf normal to said bearing portion, said ischial bearing portion of said bearing strut having a curved cross-section for imparting strength thereto, said plurality of elongated struts being secured to said support plate in a manner to define an adjustable sleeve, and an elongated support adjustably secured to said base plate.

* * * * *